(12) United States Patent
Friedman et al.

(10) Patent No.: US 6,197,305 B1
(45) Date of Patent: Mar. 6, 2001

(54) ANTI-FUNGAL COMPOSITIONS WITH PROLONGED ACTIVITY

(75) Inventors: Doron Friedman, Karme-Yosef; Orna Levin, Kfar-Neter; Yochanan Forman, Kibbutz Maabarot; Michael Friedman, Jerusalem, all of (IL)

(73) Assignee: Farmo-Nat Ltd., Ashkelon (IL)

( * ) Notice: Subject to any disclaimer, the term of this patent is extended or adjusted under 35 U.S.C. 154(b) by 0 days.

(21) Appl. No.: 09/002,925

(22) Filed: Jan. 5, 1998

(51) Int. Cl.⁷ .......................... A61K 35/78; A61K 35/64; A01N 25/00
(52) U.S. Cl. .................... 424/195.1; 424/404; 424/405; 424/435; 424/539
(58) Field of Search ............................. 424/195.1, 404, 424/405, 435, 539

(56) References Cited

U.S. PATENT DOCUMENTS

| | | | |
|---|---|---|---|
| 4,382,886 | * | 5/1983 | Sosnowski ............................ 424/539 |
| 5,385,733 | * | 1/1995 | Mankovitz ........................ 424/195.1 |
| 5,455,033 | * | 10/1995 | Silverman et al. ............... 424/195.1 |
| 5,658,584 | * | 8/1997 | Yamaguchi .......................... 424/405 |
| 5,843,467 | * | 12/1998 | Ambroziewigz ..................... 424/401 |
| 5,846,543 | * | 12/1998 | Hassler et al. .................... 424/195.1 |

OTHER PUBLICATIONS

Tyler, V. Herbs of Choice. Ther. Use of Phytomed., pp. 96–97, 157–158, 160, 164–166, 182–184, 1994.*
Vosnjak, M. The Miracles of Propolis, pp. 27–31 and 53–58, 1978*

* cited by examiner

Primary Examiner—Leon B. Lankford, Jr.
Assistant Examiner—Christopher K. Tate
(74) Attorney, Agent, or Firm—Mark M. Friedman

(57) ABSTRACT

An anti-fungal composition, including: (a) an extract of botanical materials, the botanical materials including material from Echinacea species, and Propolis, which is a material derived from the hives of bees; and (b) an essential oil. The compositions of the present invention have been shown to have unexpectedly prolonged anti-fungal activity, as well as having anti-bacterial and anti-inflammatory activities. Preferably, the essential oil includes at least one oil selected from the group consisting of tea-tree oil, thyme oil and lavander oil. Also preferably, the herbal extract includes a mixture of Calendula, poke root, Echinacea and Propolis extract.

6 Claims, 4 Drawing Sheets

ANTI-FUNGAL COMPOSITIONS WITH PROLONGED ACTIVITY

FIELD AND BACKGROUND OF THE INVENTION

The present invention relates to a combination of an herbal extract and an essential oil which shows unexpected prolonged anti-fungal activity and, more particularly, to such a combination which can exert anti-fungal activity on mucosal membranes or skin as a topical application, or within the gastrointestinal tract.

Recently, interest has been displayed in the medicinal properties of herbal preparations. Herbal preparations are considered "more natural" and are therefore viewed as less toxic by the consumer. These preparations are being sold for a number of medical indications.

For example, a combination of Echinacea (*Echinaceae angustifoliae radix*) and Plantago (*Plantago major*) is available from Dolisos Laboratoires, Israel, as "Plantspray". Plantspray is intended as a composition for oral hygiene. According to the product literature, Plantspray has anti-bacterial activity in the oral cavity and can therefore promote the general health of oral tissues, as well as cosmetic concerns such as malodorous breath. Another herbal combination, Echinacea and Propolis, is also available from Dolisos Laboratoires as "Echinacea Propolis Tabs". Propolis wax is the resinous substance found in beehives. The Echinacea and Propolis wax combination is also intended for oral hygiene.

However, although combinations of herbal extracts have enjoyed commercial success, relatively few of these combinations have demonstrated proven anti-fungal activity. Furthermore, these combinations have not displayed both prolonged anti-fungal and anti-bacterial activity. The ability to inhibit both fungal and bacterial activity is important for the control of commonly occurring multiple and mixed infections. Finally, currently available herbal preparations also lack significant anti-inflammatory activity. However, inflammation is frequently the cause of extensive discomfort in patients with either fungal or mixed fungal and bacterial infections. Thus, currently available herbal preparations lack the ability to control or alleviate both the microbial causes, as well as the symptoms, of single or mixed infections.

Fungal infections are very common in all populations of both humans and lower animals such as livestock and pets. Indeed, the natural flora in all animals includes many fungi. Fungi grow well in a neutral to slightly alkaline, humid environment. For example, many fungal disorders are associated with an increase of the normal human skin pH from about 5.5 to a higher, more alkaline value. Similarly, many mucosal membranes such as the vagina have a slightly acidic environment when healthy, which tends to become basic when infected with fungi. Thus, normally fungal populations do not grow in an uncontrolled manner because of natural checks on their growth, such as acidity of the environment.

Such fungi are only problematic when they grow in an uncontrolled manner, causing various diseases as well as extreme discomfort for the human or lower animal infected. Unfortunately, uncontrolled fungal growth often occurs for the reasons described above, making topical anti-fungal preparations the largest segment of the market for topical external products.

Once fungal populations have become uncontrolled, the resultant infection is difficult to treat successfully. Such infections are recurrent and require a prolonged treatment regimen. Furthermore, currently available anti-fungal medications do not show prolonged activity against fungal infections, which is another drawback.

There is thus a widely recognized need for, and it would be highly advantageous to have, a herbal preparation with proven prolonged anti-fungal activity, particularly for topical skin, mucosal, oral and vaginal hygiene, and with the concomitant ability to inhibit bacterial growth and relieve inflammation, which are frequently apparent in mixed and multiple microbial infections.

SUMMARY OF THE INVENTION

It is one object of the present invention to provide specific compositions with at least one essential oil with at least one herbal extract with strong anti-fungal activity. It is a further object of the present invention to provide compositions which have highly prolonged anti-fungal activity. It is yet a further object of the present invention to provide compositions which also have good anti-bacterial activity.

Unexpectedly, it has been found that specific combinations of essential oils with an herbal extract provide strong anti-fungal activity. Also unexpectedly, it has been found that the activity is highly prolonged, particularly when compared to popular or leading commercially available anti-fungal preparations. Furthermore, these compositions also have good anti-bacterial activity, thereby providing balanced total therapy against microbial infections. The prior art neither taught nor suggested that such compositions would display such strong, prolonged anti-fungal activity, nor was it taught or suggested that such compositions would additionally display strong anti-bacterial activity.

According to the present invention, there is provided an anti-fungal composition, comprising a herbal extract and an essential oil in a ratio. Preferably, the herbal extract is a tincture. More preferably, a suitable pharmaceutical carrier is included.

Preferably, the essential oil is selected from the group consisting of cinnamon oil, cajeput oil, citronella oil, eucalyptus oil, fennel oil, geranium oil, girofle oil, lavender oil, lemon oil, spearmint oil, myrte oil, origano oil, pine oil, rosemary oil, sarriette oil, thyme oil, and tea-tree oil. More preferably, the essential oil is selected from the group consisting of tea-tree oil, thyme oil and lavander oil. Even more preferably, the essential oil is present in a concentration of from about 0.1 to about 5 percent weight per weight. Most preferably, the essential oil is present at a concentration of from about 0.2 to about 2.0 percent weight per weight.

Preferably, the herbal extract includes a material selected from the group consisting of Plantago, Hypericum, Echinacea, Baptisia, Calendula, Myrrah, Phytolacca, Salvia, Catechu black, Coneflower, Krameria, Tsuga, Rosmarinus, Styrax, Crataegus, Glycerrhiza, Angelica, Krameria, Matricaria, Mallow, Propolis and Sage. More preferably, the herbal extract includes a mixture of Calendula, poke root, Echinacea and Propolis. Most preferably, the herbal extract is present in a concentration in a range of from about 1 to about 10 percent weight per weight.

According to a preferred embodiment of the present invention, the herbal extract includes a mixture of Phytolacca extract, Coneflower extract, Symphytum extract, Canendula extract, Hamamelis extract and Propolis extract, and the essential oil includes a mixture of Thyme oil and Lavender oil. Preferably, the Phytolacca extract, the Coneflower extract, the Symphytum extract, the Calendula extract, and the Hamamelis extract are each present in an amount in a range of from about 1 percent to about 10 percent weight per weight, the Propolis extract is present in an amount in a range of from about 0.1 percent to about 5 percent weight per weight, and the Thyme oil and the Lavander oil are each present in an amount in a range of from about 0.2 percent to about 2.0 percent weight per weight.

According to another embodiment of the present invention, there is provided a method of treating a subject with a fungal infection, comprising the step of administering an anti-fungal composition to the subject, the composition including a herbal extract and an essential oil in an appropriate ratio. Preferably, the fungal infection is present in a tissue selected from the group consisting of gastrointestinal tract, mucosal tissues and skin. More preferably, the mucosal tissue is selected from the group consisting of oral cavity and vagina.

According to yet another embodiment of the present invention, there is provided a mouthwash for treating a fungal infection, including: (a) a herbal extract and an essential oil in an appropriate ratio; and (b) a pharmaceutical carrier.

According to still another embodiment of the present invention, there is provided a suppository for treating a fungal infection present in a vaginal tissue, including: (a) a herbal extract and an essential oil in an appropriate ratio; and (b) a pharmaceutical carrier. The suppository can also take the form of a soap or ovules.

According to yet another embodiment of the present invention, there is provided a cream for topical treatment of a fungal infection of the skin, including: (a) a herbal extract and an essential oil in an appropriate ratio; and (b) a pharmaceutical carrier.

Hereinafter, the phrase "pharmaceutical carrier" includes any suitable or appropriate carrier for a herbal composition.

BRIEF DESCRIPTION OF THE DRAWINGS

The invention is herein described, by way of example only, with reference to the accompanying drawings, wherein.

DESCRIPTION OF THE INVENTION

Figure 1:
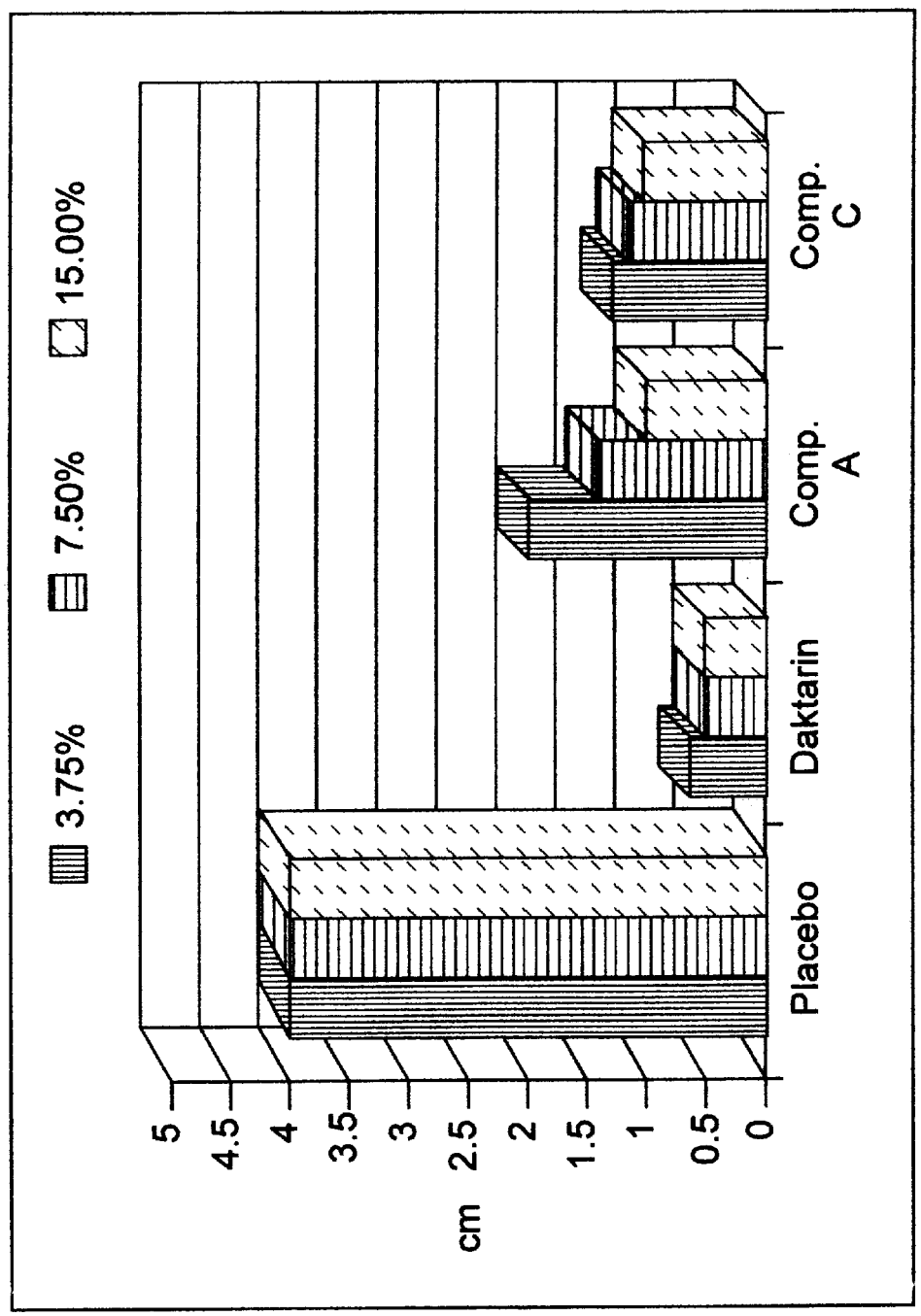
FIGS. 1 and 2 are graphs showing the prolonged anti-fungal effects of compositions of the present invention against *Aspergillus niger;*

Unexpectedly, it has been found that specific combinations of essential oils with an herbal extract provide strong anti-fungal activity. Also unexpectedly, it has been found that the activity is highly prolonged, particularly when compared to popular or leading commercially available anti-fungal preparations. Furthermore, these compositions also have good anti-bacterial activity, thereby providing balanced total therapy against microbial infections. The prior art neither taught nor suggested that such compositions would display such strong, prolonged anti-fungal activity, nor was it taught or suggested that such compositions would additionally display strong anti-bacterial activity.

The compositions of the present invention include an essential oil and a herbal extract. Preferably, the essential oil includes at least one oil selected from the group consisting of cinnamon oil, cajeput oil, citronella oil, eucalyptus oil, fennel oil, geranium oil, girofle oil, lavender oil, lemon oil, spearmint oil, myrte oil, origano oil, pine oil, rosemary oil, sarriette oil, thyme oil, and tea-tree oil. More preferably, the essential oil includes at least one oil selected from the group consisting of tea-tree oil, thyme oil and lavander oil. Also preferably, the essential oil is present in a concentration of from about 0.1 to about 5 percent weight per weight. Most preferably, the essential oil is present at a concentration of from about 0.2 to about 2.0 percent weight per weight. Preferably, the herbal extract includes a mixture of Calendula, poke root, Echinacea and Propolis extract. Most preferably, the herbal extract is present in a concentration in a range of from about 1 to about 10 percent weight per weight. Although a limited number of combinations of essential oils and herbal extracts are shown, it is contemplated that substantially any combination of these particular essential oils and herbal extracts could be efficacious.

Hereinafter, the term "host" refers to the human or lower animal infected with a fungus. The term "infected" refers to the state of having a fungus present. whether growth of the fungus is controlled or uncontrolled. The term "subject" refers to the human or lower animal to whom the compositions of the present invention are administered. The term "administered" includes, but is not limited to, such routes of introducing the composition to the subject as local oral, mucosal, topical, intra-nasal and intra-vaginal applications.

DESCRIPTION OF THE PREFERRED EMBODIMENTS

The present invention is of a composition of herbal extracts and essential oils which has anti-fungal activity. Specifically, the present invention can be used to combat fungal infection in a variety of environments, including the skin, mucosal organs and the oral cavity. These compositions also have strong anti-bacterial activity, in addition to its anti-fungal activity.

This anti-fungal composition includes two components. The first component is an essential oil and the second is a herbal extract of botanical materials, such as a tincture.

The first component can be any one of a number of different essential oils, or a mixture of two or more essential oils. An essential oil is a volatile mixture of esters, aldehydes, alcohols, ketones and terpenes, which can be prepared from botanical materials or plant cell biomass from cell culture. Examples of essential oils include, but are not limited to, oil of cinnamon, prepared from the dried bark of the roots of *Cinnamomum zeyloriaceae;* cajeput oil; eucalyptus oil, prepared from the fresh leaves and branches of various species of Eucalyptus, such as *E. globulus;* fennel oil, prepared from dried ripe fruit of *Foeniculum vulgare;* geranium oil, prepared from the aerial parts of Pelargonium species; girofle oil, lavander oil, prepared from fresh flowering tops of Lavandula species such as *Lavandula officinalis;* lemon oil, obtained from the fresh peel of *Citrus limon;* spearmint oil, prepared from the overground parts of fresh flowering Mentha species, such as *M spicata;* myrte oil, origano oil, pine oil, rosemary oil, prepared from tops or leafy twigs of *Rosmarinus officinalis;* sarriette oil, thyme oil, prepared from the leaves and flowering tops of *Thymus vulgaris;* and tea-tree oil, obtained from the leaves of *Melaleuca olternifolia.*

Essential oils can be prepared by subjecting botanical materials to a distillation process, for example. A number of different procedures can be used for distillation. One such example, using dried bark of the shoots of *Cinnamomum zeyloriaceae,* is given for illustrative purposes only and is not intended to be limiting. First, the bark is placed in a suitable still with sufficient purified water. Next, the bark is distilled with steam from the water. The steam is then condensed and the oil phase is separated from the aqueous phase to obtain the essential oil. All of the above essential oils are also available commercially. In the preparations of the present invention, the essential oils, such as cinnamon oil, contain not less than about 1.2% weight per volume of volatile oil.

The second component is a herbal extract, such as a tincture of botanical materials, which prepared by contacting botanical material with a solvent [*British Herbal Pharmacopoeia*, Peter R. Bradley, ed., British Herbal Medicine Association, 1983; and *British Herbal Compendium*, Peter R. Bradley, ed., British Herbal Medicine Association, 1992]. The solvent can be aqueous or organic, or a combination thereof. Acceptable organic solvents include, but are not limited to, glycerin, propylene glycol or alcohol, or a combination thereof. The most preferred solvents are hydroalcoholic solvents as defined in *British Herbal Pharmacopoeia and Compendium*. The botanical material can include, but is not limited to, one or more of the following species: Plantago (*Plantago major*), Hypericum (*Hypericaceae perforatus*), Echinacea (Echinaceae species such as *Echinaceae angustifoliae radix* and *Echinaceae purpurea*), Baptisia, Calendula, Myrrah, Phytolacca, Salvia, Catechu black, Krameria, Tsuga, Rosmarinus, Styrax, Crataegus, Glycerrhiza (*Glycerrhiza glabra*), Angelica, Matricaria, Mallow and Sage. The most preferred tincture of botanical material is present by combining extracts of Plantago (*Plantago major*), Hypericum (*Hypericaceae perforatus*), Echinacea (*Echinaceae angustifoliate radix*) and Propolis, which is the resinous substance found in beehives. Although strictly speaking Propolis is not a botanical material, extracts of this material are prepared in a substantially similar manner as extracts of the plant materials. These extracts can be prepared according to one of the following methods, although of course other methods could be used, and are also available commercially.

In the first method, the botanical materials are macerated with a solvent. The solvent is allowed to remain in contact with the botanical materials for an appropriate period of time and is then filtered to remove solid or particulate material in order to form a filtered extract. If desired, additional solvent can be added to the filtered extract to bring it to a final volume. Alternatively, solvent can be evaporated to increase the concentration of the active constituents of the extract.

In the second method, the botanical materials are percolated with a solvent. The botanical materials are placed in a column, known as a percolator. The solvent is then allowed to flow through the column, contacting the botanical methods, and is collected. The collected solvent forms the extract. Percolation has the advantage of allowing a minimal volume of solvent to be used during the extraction process. The volume of solvent required can be partially controlled by the rate of fluid flow through the column, allowing for greater control over the final volume of extract. Preferably, the flow of solvent out of the column is stopped entirely during extraction, so that the efficiency of extraction is increased. This represents a combination of maceration and percolation.

If either method, or a combination of both methods, is used to prepare extracts of the above botanical materials, preferably alcoholic or hydroalcoholic solvents are used. Most preferably, the botanical materials are harvested no more than 24 hours previously, so that these materials are fresh.

In the present invention, these extracts of the botanical materials were used directly as tinctures. Hereinafter, the term "tincture" refers to an extract of either the botanical materials or of Propolis, prepared substantially as described above.

EXAMPLE 1

Anti-Fungal Effects of Compositions of the Present Invention

A composition of the present invention was tested for its effect against fungal activity. The composition included 4.6% Phytolacca extract, 4.6% Coneflower extract, 3.1% Symphytum extract, 3.1% Calendula extract, 3.1% Hamamelis extract, 1.5% Propolis extract, 0.5% Thyme oil and 0.5% Lavender oil, as the active ingredients. Two different fungal species were tested, *Candida albicans* and *Aspergillus niger*. These fungi were grown in a suitable solid growth medium, TSA (Difco, Detroit, Mich., USA) to which 10%, 5%, 2.5%, 1.25% of either the composition or alcohol (as a control) was added. As a further control, fungi were also grown without the addition of either the alcohol alone or the composition. Results are shown in Table 1 below.

TABLE 1

Inhibitory Effect of the First and Second Anti-fungal Compositions

| | | Concentration of Anti-fugal Composition | | | | |
|---|---|---|---|---|---|---|
| Substance | Fungus | Control | 1.25% | 2.5% | 5% | 10% |
| alcohol | Candida | + | + | + | + | – |
| alcohol | Aspergillus | 3.7 mm | 3.1 mm | 2.6 mm | 2.0 mm | 0.5 mm |
| composition | Candida | + | + | + | – | – |
| composition | Aspergillus | 3.7 mm | 3.8 mm | 2.5 mm | 0.5 mm | – |

As shown in Table 1, alcohol alone did slightly inhibit the growth of *Candida albicans*, with a MIC of 10%. As noted above, MIC is the minimal inhibitory concentration, which is the lowest concentration of a substance which measurably inhibits growth of the micro-organism. Alcohol alone also reduced, but did not completely inhibit, the growth of *Aspergillus niger*.

The test composition strongly inhibited the growth of *Candida albicans*, with a MIC of 5%. In addition, the test composition strongly inhibited the growth of *Aspergillus niger*. Thus, this composition shows clear anti-fungal properties, due to the combination of the essential oil and the tincture.

In addition, two other formulas were tested against a standard, currently available fungicidal compound (Daktarin; active ingredient, miconazole; available from Abic Ltd., Israel), as well as against a placebo (no treatment). The formulas of the compositions were as follows:

| Ingredient | % W/W |
|---|---|
| Composition A | |
| Water | 54.0 |
| Safflower oil | 10.0 |
| Beeswax | 5.0 |
| Cetearyl Octanoate | 5.0 |

-continued

| Ingredient | % W/W |
| --- | --- |
| Cetearyl Glucoside | 5.0 |
| Glycerin | 5.0 |
| Poke Root (*Phytolacca Decandra*) extract | 4.0 |
| *Calendula officinalis* extract | 4.0 |
| Coneflower (*Echinacea Purpurea*) extract | 2.0 |
| Propolis extract | 2.0 |
| Tea-Tree (*Melaleuca Olternifolia*) oil | 1.0 |
| Thyme Oil | 1.0 |
| Polyacrylamide/C13–14 isoparaffin/lauret-7 | 1.0 |
| Sodium lactate | 0.7 |
| Lactic Acid | 0.3 |
| Composition B | |
| Water | 30.08 |
| Ethyl Alcohol | 35.08 |
| Propylene Glycol | 12.0 |
| Polyethylene glycol 400 | 8.0 |
| Poloxamer 188 | 4.0 |
| Phytolacca extract | 2.3 |
| Coneflower extract | 2.3 |
| Symphytum extract | 1.6 |
| Calendula extract | 1.6 |
| Hamamelis extract | 1.6 |
| Propolis extract | 0.8 |
| Sodium lauryl sulfate | 0.2 |
| Thyme oil | 0.2 |
| Lavander oil | 0.2 |
| Ethylenediaminetetra-acetic acid disodium salt | 0.02 |
| a-Tocopherol Acid Succinate | 0.02 |
| Composition C | |
| Water | 48.0 |
| Safflower oil | 10.0 |
| Beeswax | 5.0 |
| Cetearyl octanoate | 5.0 |
| Cetearyl glucoside | 5.0 |
| Glycerol | 5.0 |
| Phytolacca extract | 4.6 |
| Coneflower extract | 4.6 |
| Symphytum extract | 3.1 |
| Calendula extract | 3.1 |
| Hamamelis extract | 3.1 |
| Propolis extract | 1.5 |
| Polyacrylamide/C13–14 isoparaffin/lauret-7 | 1.0 |
| Thyme oil | |
| Lavander oil | 0.5 |

These compositions were tested by evaluating the diameter (cm) of *Aspergillus niger* colonies which formed on a plate treated with one of the following: Composition A or C, the standard anti-fungal compound, Daktarin, or a placebo. The colonies were grown on solid TSA media. Colony growth was evaluated in a blind test, in which the researcher was not aware of the identity of the sample. The results are given in FIG. 1A. Essentially, the compositions of the present invention were able to strongly inhibit fungal growth. Composition A was particularly able to inhibit such growth, to an extent which is on a par with the commercially available formulation.

Figure 2:
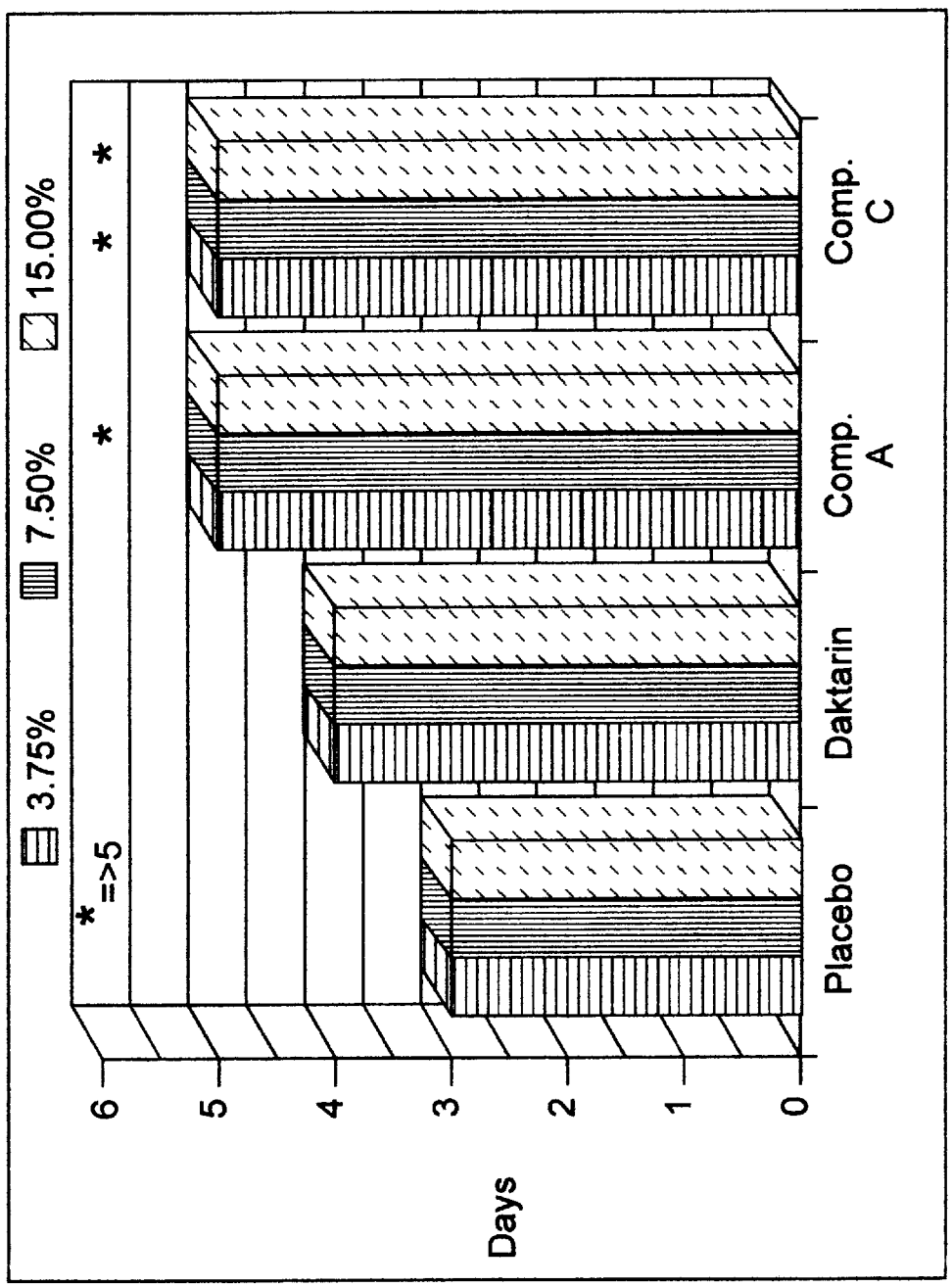

In addition, the compositions were evaluated for their ability to inhibit sporulation of *Aspergillus niger*. The fungi were grown as described above, on media which was treated with Composition A or C, or with Daktarin or a placebo. The results are shown in FIG. 2. Fungi treated with placebo (inert vehicle) sporulated after 3 days. Fungi treated with Daktarin took only one day longer to sporulate, which is generally the effect reported in the literature for anti-fungal agents. However, fungi treated with Composition A took five days to sporulate, while fungi treated with Composition C showed only very weak sporulation after five days, when the experiment was ended. Thus, clearly the compositions of the present invention are able to inhibit sporulation for a greater length of time than one of the most frequently used, commercially available fungicidal medications.

Figure 3:
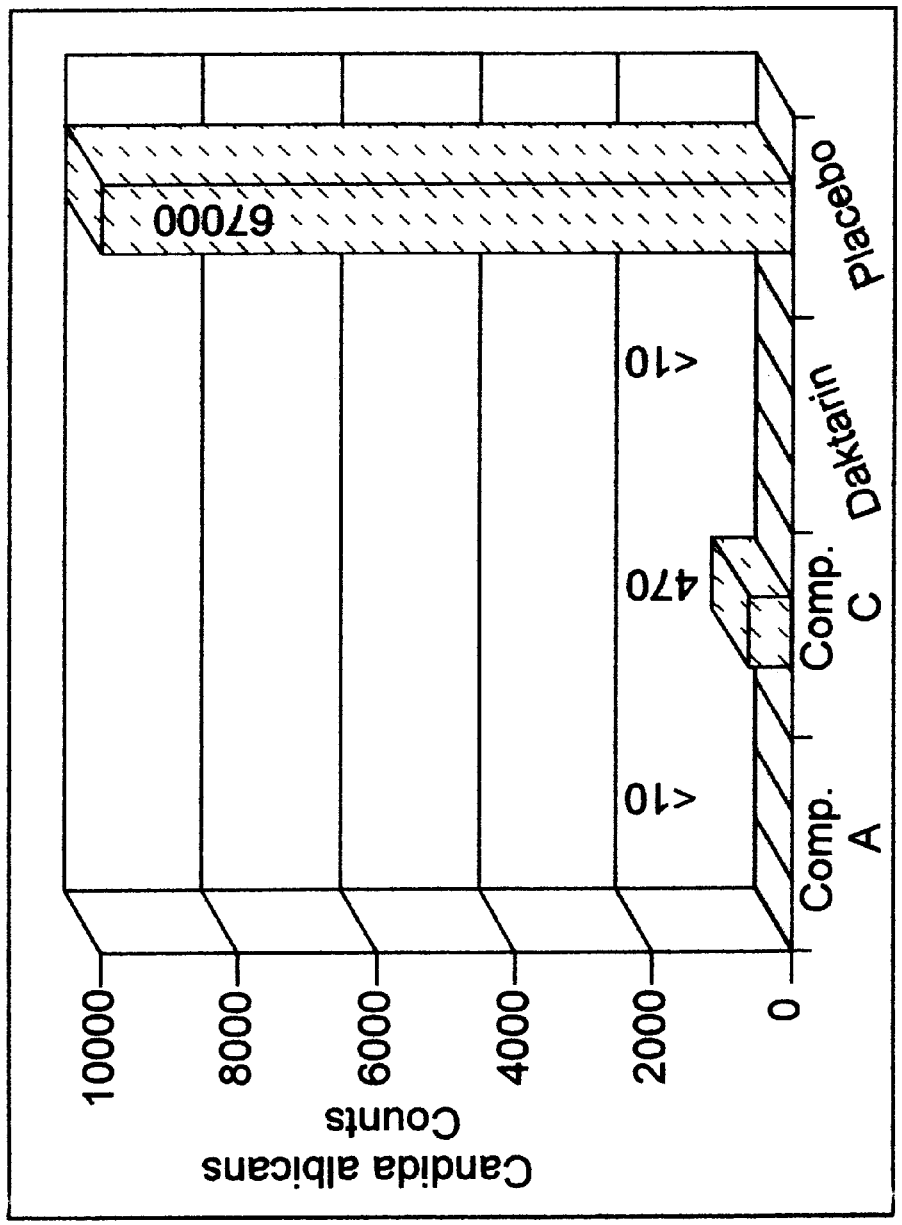
FIG. 3 shows the effect of anti-fungal compositions of the present invention against *Candida albicans.

The anti-fungal activity of Compositions A and B was also tested against *Candida albicans*. These compositions were tested by determining the number of *C. albicans* microorganisms which grew in a solution treated with one of the following: Composition A or B, the standard commercially available anti-fungal compound, Daktarin, or a placebo. The microorganisms were grown in liquid media and growth was evaluated in a double-blind test. The results are given in FIG. 3, in which "counts" refers to the number of *C. albicans* microorganisms in the sample. Essentially, the compositions of the present invention were able to strongly inhibit fungal growth. Composition A was particularly able to inhibit such growth, to an extent which is on a par with the commercially available formulation.

Figure 4:
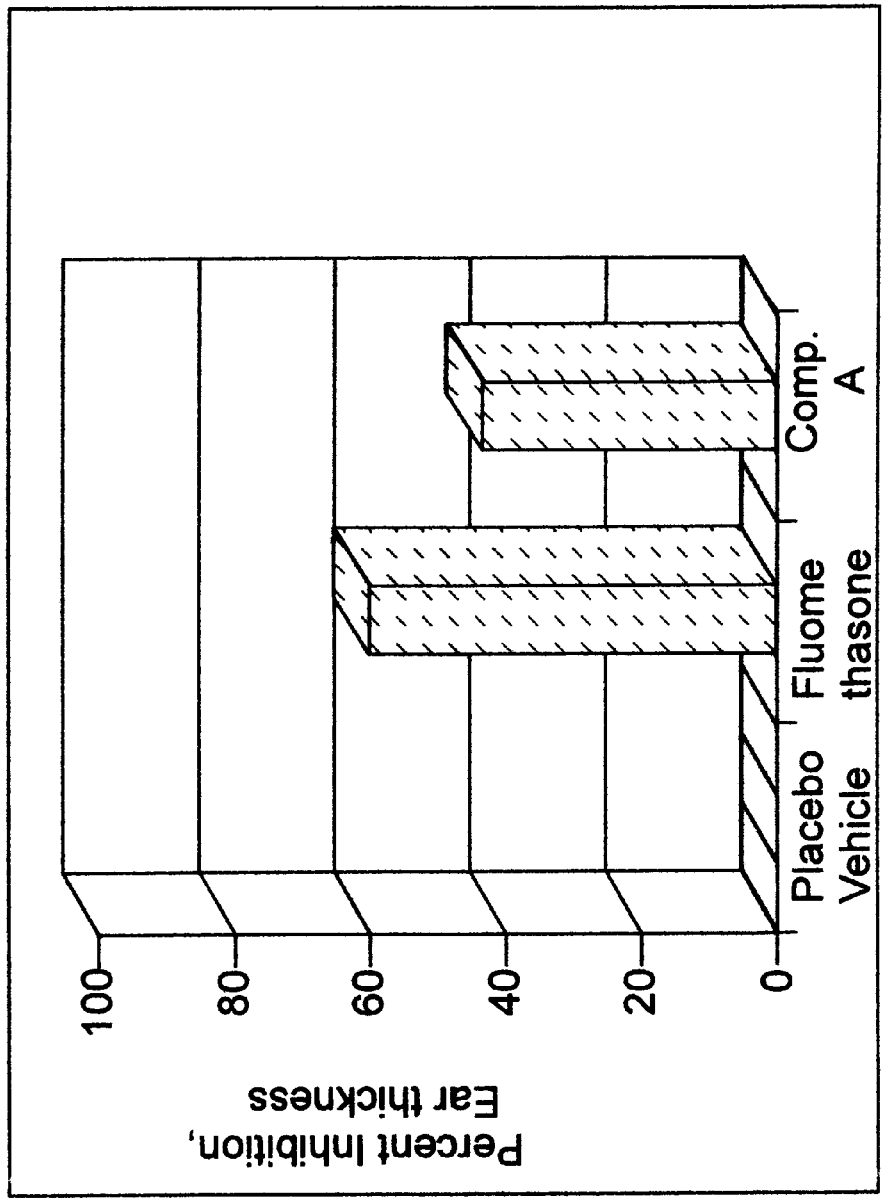
* and FIG. 4 shows the anti-inflammatory effect of a composition of the present invention.

Finally, Composition B was tested for its anti-inflammatory activity in a tissue sensitized with crotton oil. The sensitized tissue examined was the ear of a rat. The ear thickness was measured with a micrometer to determine the degree of inflammation, which was directly proportional to the thickness of the ear. The tissue was treated with placebo, fluomethasone (a commercially available anti-fungal agent; available as "Dermalar" from Teva Ltd., Israel) or with Composition B. FIG. 4 shows the extent of inhibition of inflammation, as a percent of the untreated tissue. Thus, higher values on the vertical axis show that the ear thickness was reduced, indicating an inhibition of inflammation.

As FIG. 4 demonstrates, placebo alone was not able to inhibit inflammation. Fluomethasone and Composition B both inhibited inflammation to a similar extent, reducing it by about 50%. Thus, clearly the compositions of the present invention can inhibit inflammation associated with a fungal infection, thereby reducing the pain and discomfort associated with such infections.

In addition, these compositions were also noted for their anti-fungal effect when tested on the skin of human patients in topical formulations, as well as in a formulation to combal fungal infections of the nails. Furthermore, these compositions substantially lacked toxicity in these patients (data not shown).

Although this composition is described as an "anti-fungal composition" for the sake of clarity, it is understood that such a designation is not intended as a limitation and that this composition has many other uses as a treatment for various diseases and conditions, as further described in Example 4 below.

EXAMPLE 2

Anti-Fungal Effects of Separated Components of Compositions of the Present Invention A composition of the present invention, either complete or with one component removed, was tested for the effect against fungal activity. As for Example 1, the composition included 4.6% Phytolacca extract, 4.6% Coneflower extract, 3.1% Symphytum extract, 3.1% Calendula extract, 3.1% Hamamelis extract, 1.5% Propolis extract, 0.5% Thyme oil and 0.5% Lavander oil as the active ingredients. One fungal species was tested, Aspergillus niger. The fungi were grown in a suitable solid growth medium, TSA (Difco, Detroit, Mich., USA) to which 15%, 7.5% or 3.75% of the composition, the composition with one component removed, the commercially available anti-fungal agent Daktarin or alcohol (as a control) was added. Both colony diameter was measured, in centimeters (cm), and the presence or absence of sporulation five days after the addition of the test substance. Results are shown in Table 2 below.

TABLE 2

Inhibitory Effect of the Tested Substance

| | Concentration of Tested Substance | | | | | |
|---|---|---|---|---|---|---|
| | Colony diameter (cm) | | | Presence (+)/Absence(−) of Sporulation | | |
| Substance | 15% | 7.5% | 3.75% | 15% | 7.5% | 3.75% |
| alcohol | 3.5 | 3.5 | 3.5 | + | + | + |
| Daktarin | 0.25 | 0.30 | 0.50 | + | + | + |
| no Propolis | 1.75 | 2.25 | 2.40 | − | − | + |
| no extract | 1.45 | 2.00 | 2.40 | − | − | + |
| no oil | 3.50 | 3.50 | 3.50 | + | + | + |
| complete composition | 1.50 | 1.80 | 2.10 | − | − | + |

As shown in Table 2, alcohol alone did not substantially alter the growth of *Aspergillus niger*. The complete composition, however, did strongly inhibit the growth of *Aspergillus niger*. Interestingly, the essential oils (Thyme and Lavander oils) appear to have contributed the majority of the anti-fungal effect of this composition, since removing the essential oil substantially eliminated the anti-fungal effect of the composition, or at least reduced the effect to the level of alcohol alone. Propolis appears to be the next most important ingredient, followed by the herbal extract (Phytolacca extract, Coneflower extract, Symphytum extract, Calendula extract and Hamamelis extract). Although Propolis is known to have some intrinsic anti-fungal activity, the results clearly show that the complete composition has much more significant anti-fungal activity than Propolis alone. Furthermore, both the complete composition and the other compositions which contained essential oils were able to significantly inhibit sporulation at 5 days after addition of the test substance, unlike the commercially available Daktarin. Thus, this composition shows clear anti-fungal properties, in particular the ability to inhibit sporulation, largely due to the presence of the essential oils.

EXAMPLE 3

Anti-fungal Preparations and Methods of Administration

As noted above, combinations of a tincture and an essential oil show strong, prolonged anti-fungal activity. These combinations can be used in a number of formulations. Furthermore, these formulations can be administered to a subject in a number of ways, which are well known in the art. For example, administration may be done topically (including ophtalmically, vaginally, rectally, intranasally), locally in the oral cavity or by inhalation.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable. The suppository can also take the form of a soap or ovules.

Compositions for local oral administration may be prepared in a similar fashion, in the form of toothpastes, creams, ointments, gels, aqueous solution, other liquid solutions and lotions. Chewing tablets may also be employed, in which tablets are formulated to deliver the compositions of the present invention while being chewed by the subject.

Dosing is dependent on the severity of the symptoms and on the responsiveness of the patient to the composition. Persons of ordinary skill in the art can easily determine optimum dosages, dosing methodologies and repetition rates.

EXAMPLE 4

Methods of Treatment with the Compositions of the Present Invention

The compositions of the present invention, which include an effective amount of an essential oil and of a tincture, as described above, can be used to treat a number of different diseases and conditions. For example, these compositions can be used in a mouthwash, for oral hygiene, as described in Example 5 below, as well as in a topical formulation for skin treatment, as described in Example 7.

These compositions can also be used to treat bacterial infections of other body tissues, such as bacterial infections of the skin including, but not limited to, impetigo, folliculitis, acne and furuncolosis, and bacterial infections of mucous membranes such as vaginal tissue, anal tissue, oral cavity tissue, tissue of other orifices and ocular tissue. Fungal, viral and parasitic infections may also be treated.

In addition, conditions which are not the direct result of infection by an infectious agent, such as a bacterium, virus, fungus or parasite, can also be treated with the compositions of the present invention. Such conditions include the sites of insect bites, first-degree burns and areas of general inflammation, with or without the presence of an infectious agent.

The following is a general list of other diseases and conditions which can be treated with the compositions of the present invention. It is intended for illustrative purposes only and is not meant to be limiting. The diseases and conditions include: psoriasis, *Herpes zoster* infection, contact dermatitis, Condyloma catum, atopic eczema, seborrhea, Varicella infection, pemphigus, Varicola infection, Verruca, seborrheic dermatitis or keratosis, ulcers, *Herpes simplex* infection, glossitis, dental ulcers, stomatitis, aphthous ulcers, leukoplakia, abscesses, skin wounds and inflammation, primary and secondary skin infections including, but not limited to, varicose ulcers and contagiosa, diaper rash, skin irritation, eczema dermatos, itching, pruritis, urticaria, ichthyosis, hyperkeratotic skin, allergic dermatitis and infected eczema.

EXAMPLE 5

Mouthwash for Oral Hygiene

Hygiene of the oral cavity is important for dental care, as well as for overall good health. In patients with compromised immune systems, hygiene of the oral cavity is even more important, since these patients are vulnerable to extremely painful, debilitating fungal infections in these tissues. In these patients, inhibition of fungal growth can be accomplished by rinsing of the oral cavity with a mouthwash solution.

As noted in the Background section above, simply finding anti-fungal activity of a herbal preparation is not sufficient for its use as a medicine. Like all medicines, the herbal preparation must be used in a manner which is safe and effective. Given both the apparent safety and the effectiveness of the anti-fungal preparations in the treatment of human patients, the following mouthwash formulation of a combination of an essential oil and a tincture for oral hygiene were prepared. This formulation is intended as an illustrative example only and is not intended to be limiting in any way.

The following procedure was used to prepare the mouthwash. All percentages are given as percent weight per weight. The active ingredients in the mouthwash are an essential oil and a tincture which show anti-bacterial and anti-fungal activity. Although other ingredients may show such activity, it is secondary to their other functions. Hence, these other ingredients are described as forming the pharmaceutical carrier for the two active, anti-fungal and anti-bacterial ingredients.

The remaining ingredients preferably include alcohol, present in a concentration of from about 0% to about 25%, preferably from about 5% to about 15%. Alcohol contributes to the activity of the mouthwash, as well as enhancing flavor and providing a refreshing sensation in the oral cavity. Another preferred ingredient is flavor, added to make the mouthwash more pleasant to use and to cosmetically enhance breath aroma. A third preferred ingredient is fluoride, which has anti-caries activity. A fourth preferred ingredient is a surfactant, which can solubilize flavors, aid removal of debris from the oral cavity and even provide anti-bacterial activity. Surfactants can be cationic, such as cetylpyridinium chloride; anionic, such as sodium lauryl sulfate, for example; Tween, Pluronic or any other food or pharmaceutical grade surfactant. A fifth preferred ingredient is a humectant, such as glycerin, sorbitol and hydrogenated starch hydrolyzates, which are often added to provide body or viscosity to the mouthwash, as well as a sweet taste. A sixth preferred ingredient is an astringent salt, which forms a thin protective film on the oral mucosa, reducing the permeability of the mucosal cells. Zinc chloride is an example of such an astringent salt, which is considered safe for topical application to the oral mucosa and is therefore often used in mouthwashes.

One example of a preferred formulation is given in Table 3 below. This formulation is intended for illustrative purposes only and is not intended to be limiting. In this example, the tincture includes the extracts of Plantago, Hypericum, Coneflower and Propolis and the essential oil is cinnamon oil.

TABLE 3

Formulation of a Mouthwash with Tincture and Cinnamon Oil

| Ingredient | Percent (weight per weight) |
| --- | --- |
| water | 75.47 |
| propylene glycol | 10 |
| ethyl alcohol | 7.5 |
| polysorbate 80 | 1.8 |
| Plantago extract | 1.5 |
| Hypericum extract | 1.5 |
| Coneflower extract | 1.0 |
| Propolis extract | 1.0 |
| Cinnamon oil | 0.2 |
| Saccharin sodium salt | 0.03 |

The preferred method of preparing the mouthwash of the above formulation was as follows. First, propylene glycol and ethanol are mixed to form a mixture. Next, polysorbate 80 was added to the mixture. Cinnamon oil was then added and the entire mixture was preferably mixed for about ten minutes.

One by one, each extract of the tincture was added in any order. Thus, Plantago extract, Hypericum extract, Coneflower extract and Propolis extract were combined with the mixture to form a combination. After each addition, the mixture was preferably mixed for about ten minutes.

Next, water and a 0.3% solution of saccharin sodium salt was preferably added to the combination with stirring to form the mouthwash.

EXAMPLE 6

Oral Gel

Another formulation for administration of the compositions of the present invention to the oral cavity is as an oral gel. The following formulation is intended as an example only and is not meant to be limiting in any way.

TABLE 4

Formulation of an Oral Gel

| Ingredient | Percent (Weight per Weight) |
| --- | --- |
| Water | 14.37 |
| PEG 75 | 20.0 |
| PEG 8 | 20.0 |
| Poloxamer 407 | 20.0 |
| Propylene Glycol | 8.0 |
| Polyacrylamide/C13–14 Isoparaffin/lauret-7 | 6.0 |
| Phytolacca Extract | 3.0 |
| Calendula Extract | 3.0 |
| Coneflower Extract | 2.0 |
| Propolis Extract | 2.0 |
| Tea-tree Oil | 0.6 |
| Ethyl alcohol | 0.5 |
| Tocopherol succinate | 0.3 |
| EDTA | 0.2 |
| Saccharin sodium salt | 0.03 |

EXAMPLE 7

Skin Cream

The compositions of the present invention can also be used for topical treatment of skin disorders and infections. The following formulation, given in Table 5, is intended as an example only and is not intended to be limiting.

TABLE 5

Skin Cream

| Ingredient | Percent Weight per Weight |
| --- | --- |
| Water | 48.0 |
| Safflower Oil | 10.0 |
| Beeswax | 5.0 |
| Cetearyl octanoate | 5.0 |
| Cetearyl glucoside | 5.0 |
| Glycerol | 5.0 |
| Phtolacca Extract | 4.6 |
| Coneflower Extract | 4.6 |
| Symphytum Extract | 3.1 |
| Calendula Extract | 3.1 |
| Hamamelis Extract | 3.1 |
| Propolis Extract | 1.5 |
| Polyacrylamide/C13–14 Isoparaffin/lauret-7 | 1.0 |
| Thyme Oil | 0.5 |
| Lavender Oil | 0.5 |

EXAMPLE 8

Cream

A second example of a formulation with a composition of the present invention for the treatment of skin disorders such as impetigo and related infections is given below. The following formulation, given in Table 6, is intended as an example only and is not intended to be limiting.

TABLE 6

Cream

| Ingredient | Percent Weight per Weight |
|---|---|
| Water | 54.0 |
| Caprylic/Capric triglyceride | 10.0 |
| Beeswax | 5.0 |
| Cetearyl octanoate | 5.0 |
| Cetearyl glucoside | 5.0 |
| Glycerine | 5.0 |
| Burdock Extract | 4.0 |
| Coneflower Extract | 3.0 |
| Baptisia Extract | 2.0 |
| Myrrh Extract | 2.0 |
| Propolis Extract | 2.0 |
| Polyacrylainide/C13–14 Isoparaffin/lauret-7 | 1.0 |
| Thyme Oil | 1.0 |
| Sweet Marjoram Oil | 1.0 |

EXAMPLE 9

Skin Gel

Another example of a formulation with a composition of the present invention for the treatment of skin disorders is in the form of a skin gel. The following formulation, given in Table 7, is intended as an example only and is not intended to be limiting.

TABLE 7

Skin Gel

| Ingredient | Percent Weight per Weight |
|---|---|
| Water | 68.75 |
| PEG 8 | 7.0 |
| Chickweed Extract | 2.0 |
| Cetearyl octanoate | 6.0 |
| Calendula Extract | 2.0 |
| Witch Hazel Extract | 2.0 |
| Burdock Extract | 3.0 |
| Comfrey Extract | 2.0 |
| Baptisia Extract | 2.0 |
| Ethyl Alcohol | 0.75 |
| Tocopheryl Succinate | 0.5 |
| Polyacrylamide/C13–14 Isoparaffin/lauret-7 | 4.0 |
| Thyme Oil | 0.5 |
| Sweet Marjoram Oil | 0.5 |

EXAMPLE 10

Other Formulations for Anti-fungal Activity

The following are examples of formulations for compositions with anti-fungal activity. These formulations have a variety of textures and consistencies, and are suitable for a number of applications. These formulations are intended as examples only and are not meant to be limiting in any way.

| Ingredient | % W/W |
|---|---|
| Composition D | |
| Water | 74.97 |
| Propylene Glycol | 10.0 |
| Ethyl Alcohol | 7.5 |
| Polysorbate 80 | 1.8 |
| Baptisia extract | 1.5 |
| Coneflower extract | 1.0 |
| Silvia extract | 1.0 |
| Myrrha extract | 1.0 |
| Propolis extract | 1.0 |
| Thyme oil | 0.2 |
| Saccharin sodium salt | 0.03 |
| Composition E | |
| Water | 75.77 |
| Propylene Glycol | 10.0 |
| Ethyl Alcohol | 7.5 |
| Polysorbate 80 | 1.8 |
| Phytolacca extract | 1.5 |
| Calendula extract | 1.5 |
| Coneflower extract | 1.0 |
| Propolis extract | 1.0 |
| Tea-Tree oil | 0.2 |
| Saccharin sodium salt | 0.03 |
| Composition F | |
| water | 61.83 |
| Silica | 20.0 |
| Glycerin | 10.0 |
| Carrageenan (*Chondrus crispus*) | 1.6 |
| Sodium lauryl sulfate | 1.4 |
| Myrrh (*Commiphora myrrha*) extr. | 1.0 |
| Plantain (*Plantago major*) extr. | 0.6 |
| *Hypericum perforatum* extr. | 0.6 |
| Cinnamon (*Cinnamon cassia*) oil | 0.5 |
| Ethy alcohol | 0.5 |
| Coneflower (*Echinacea purpurea*) | 0.4 |
| Propolis extract | 0.4 |
| Menthol | 0.4 |
| Tea-Tree (*Melaleuca alternifolia*) oil | 0.2 |
| Tocopherol succinate | 0.2 |
| EDTA disodium salt | 0.2 |
| Sodium fluoride | 0.15 |
| Natural green 5 | 0.02 |
| Composition G | |
| Propylene Glycol | 10.0 |
| Ethyl Alcohol | 7.5 |
| Polysorbate 80 | 1.8 |
| Plantago extract | 1.5 |
| Hypericum extract | 1.5 |
| Coneflower extract | 1.0 |
| Propolis extract | 1.0 |
| Cinnamon oil | 0.2 |
| Saccharin sodium salt | 0.03 |
| Composition H | |
| Water | 68.75 |
| PEG 8 | 7.0 |
| Cetearyl octanoate | 6.0 |
| Polyacrylamide/C13–14 isoparaffin/lauret-7 | 4.0 |
| Burdock (*Arctium lappa*) extract | 3.0 |
| Chickweed (*Stellaria media*) extract | 3.0 |
| *Calendula officinalis* extract | 2.0 |
| Witch Hazel (*Hamamelis virginiana*) extract | 2.0 |
| Confrey (*Symphytum officinale*) extract | 2.0 |
| Ethyl Alcohol | 0.75 |
| Thyme (*Thymus vulgaris*) oil | 0.5 |
| Sweet Marjoram (*Origanum marjorana*) oil | 0.5 |
| Tocopheryl Succinate | 0.5 |
| Composition I | |
| Water | 54.0 |
| Caprylic/Capric triglyceride | 10.0 |
| Beeswax | 5.0 |
| Cetearyl octanoate | 5.0 |
| Cetearly glucoside | 5.0 |
| Glycerine | 5.0 |
| Burdock (*Arctium lappa*) extract | 4.0 |
| Coneflower (*Echinacea purpurea*) extract | 3.0 |

-continued

| Ingredient | % W/W |
| --- | --- |
| Wild Indigo (*Baptisia tinctoria*) extract | 2.0 |
| Propolis extract | 2.0 |
| Myrrh (*Commiphora myrrha*) extract | 2.0 |
| Thyme (*Thymus vulgaris*) oil | 1.0 |
| Sweet Marjoram (*Origanum marjorana*) oil | 1.0 |
| Polyacrylamide/C13–14 Isoparaffin/Laureth-7 | 1.0 |
| Composition J | |
| Water | 65.0 |
| Harpagophytum extract | 8.0 |
| PEG 8 | 7.0 |
| Cetearyl octanoate | 7.0 |
| Hammamelis extract | 5.0 |
| Polyacrylamide/C13–14 isoparaffin/Laureth-7 | 4.0 |
| Arnica extract | 3.0 |
| Lavender oil | 1.0 |
| Rosmarinus oil | 1.0 |

While the invention has been described with respect to a limited number of embodiments, it will be appreciated that many variations, modifications and other applications of the invention may be made.

What is claimed is:

1. A composition for oral hygiene for treating a fungal infection, comprising:
   (a) a mixture of herbal extracts comprising Propolis extract, Phytolacca extract, Echinacea extract, Symphytum extract, Calendula extract and Hamamelis extract;
   (b) a mixture of essential oils comprising Thymus oil and Lavandula oil; and
   (c) a pharmaceutical carrier;
   wherein said herbal extracts are each present in an amount of from about 1% to about 10% by weight, and each essential oil is present in an amount of from about 0.2% to about 2.0% by weight.

2. The composition according to claim 1, wherein said pharmaceutical carrier is in a form selected from the group consisting of mouthwash, toothpaste and tablet.

3. The composition according to claim 1, wherein at least one herbal extract is in a form of a tincture.

4. The composition according to claim 1, further comprising:
   (d) an additional herbal extract selected from the group consisting of Plantago extract and Hypericum extract, wherein said additional herbal extract is present in an amount of from about 1% to about 10% by weight.

5. The composition according to claim 1, further comprising:
   (d) an additional essential oil selected from the group consisting of Cinnamomum oil and *Melaleuca alternifolia* oil, wherein said additional essential oil is present in an amount of from about 0.2% to about 2.0% by weight.

6. The composition according to claim 5, wherein said additional essential oil is *Melaleuca alternifolia* oil.

* * * * *